US010002425B2

(12) United States Patent
Shih et al.

(10) Patent No.: US 10,002,425 B2
(45) Date of Patent: Jun. 19, 2018

(54) METHOD OF SEGMENTING SINGLE NEURON IMAGES WITH HIGH-DYNAMIC-RANGE THRESHOLDS AND COMPUTER READABLE STORAGE MEDIUM THEREOF

(71) Applicants: National Tsing Hua University, Hsinchu (TW); Tunghai University, Taichung (TW); National Applied Research Laboratories, Taipei (TW)

(72) Inventors: Chi-Tin Shih, Taichung (TW); Nan-Yow Chen, Hsinchu (TW); Ann-Shyn Chiang, Hsinchu (TW)

(73) Assignees: National Tsing Hua University, Hsinchu (TW); Tunghai University, Taichung (TW); National Applied Research Laboratories, Taipei (TW)

( * ) Notice: Subject to any disclaimer, the term of this patent is extended or adjusted under 35 U.S.C. 154(b) by 0 days. days.

(21) Appl. No.: 15/369,897

(22) Filed: Dec. 6, 2016

(65) Prior Publication Data
US 2018/0018767 A1    Jan. 18, 2018

(30) Foreign Application Priority Data
Jul. 12, 2016   (TW) .............................. 105121971 A

(51) Int. Cl.
*G06T 7/00* (2017.01)
*G06T 17/20* (2006.01)
(Continued)

(52) U.S. Cl.
CPC ............ *G06T 7/0012* (2013.01); *A61B 6/501* (2013.01); *G06T 7/0081* (2013.01); *G06T 7/11* (2017.01);
(Continued)

(58) Field of Classification Search
None
See application file for complete search history.

(56) References Cited

U.S. PATENT DOCUMENTS

| 7,711,165 B2 * | 5/2010 | Lesage ...................... G06T 7/60 |
| | | 128/920 |
| 2002/0168110 A1 * | 11/2002 | Al-Kofahi ................ G06K 9/48 |
| | | 382/199 |

(Continued)

OTHER PUBLICATIONS

Chi-Tin Shih, NeuroRetriever: Automatic single-neuron reconstruction from fluorescent images, ACENS Conference Program, Feb. 2, 2016, ISBN 978-986-5654-34-4, Fukuoka, Japan.

*Primary Examiner* — Utpal Shah
(74) *Attorney, Agent, or Firm* — Chih Feng Yeh; Huntington IP Consulting Co., Ltd.

(57) ABSTRACT

The method of segmenting single neuron images with high-dynamic-range thresholds of the present invention includes (a) preparing a biological tissue sample containing neurons and performing imaging to this sample to obtain a three-dimensional raw neuroimage; (b) deleting voxels in the three-dimensional raw neuroimage with signal intensities below a first signal intensity threshold to obtain a first thresholded image; (c) tracing the first thresholded image to obtain a first traced image; (d) calculating a structural importance score of every voxel in the first traced image to obtain a first structural importance score of every voxel; (e) gradually increasing the signal intensity threshold and repeating (b), (c) and (d) n−1 times; (f) summing up all the n structural importance scores of every voxel; (g) deleting voxels with summed structural importance score smaller than a pre-determined value from the raw image to obtain the segmented single neuron.

14 Claims, 6 Drawing Sheets

(51) Int. Cl.
*G06T 7/136* (2017.01)
*A61B 6/00* (2006.01)
*G06T 7/11* (2017.01)

(52) U.S. Cl.
CPC .............. *G06T 7/136* (2017.01); *G06T 17/20* (2013.01); *G06T 2207/30016* (2013.01); *G06T 2207/30024* (2013.01); *G06T 2210/41* (2013.01)

(56) References Cited

U.S. PATENT DOCUMENTS

| | | | |
|---|---|---|---|
| 2011/0157177 A1* | 6/2011 | Chen ..................... | G06T 7/0081 345/424 |
| 2011/0292047 A1* | 12/2011 | Chang ................ | G06K 9/00201 345/424 |
| 2012/0323108 A1* | 12/2012 | Carroll ................. | G06T 7/0014 600/407 |

* cited by examiner

50 preparing a biological tissue sample containing neurons and performing single three-dimensional imaging to the biological tissue sample containing neurons to obtain a single raw three-dimensional neuroimage ⸺ 501 filtering out voxels in the raw three-dimensional neuroimage whose signal intensities are below a first signal intensity threshold, a second signal intensity threshold,..., a n-th signal intensity threshold respectively by the filtering module to obtain a first filtered image, a second filtered image,..., a n-th filtered image ⸺ 502 tracing the first filtered image, the second filtered image,..., the n-th filtered image for their skeleton by the tracing module respectively to obtain a first traced image, a second traced image,..., a n-th traced image ⸺ 503

Fig. 5A

METHOD OF SEGMENTING SINGLE NEURON IMAGES WITH HIGH-DYNAMIC-RANGE THRESHOLDS AND COMPUTER READABLE STORAGE MEDIUM THEREOF

CROSS-REFERENCE TO RELATED APPLICATION

The present application claims the benefit of TAIWAN Patent Application Serial Number 105121971 filed on Jul. 12, 2015, which is herein incorporated by reference in its integrity.

TECHNICAL FIELD

The present invention relates to neuron segmentation, and particularly to a method of segmenting single neuron images with high-dynamic-range thresholds and a computer readable storage medium thereof.

BACKGROUND OF RELATED ARTS

Connectome assembled with three-dimensional images of single neurons obtained via three-dimensional imaging of neuro-tissue is regarded as an important step to understand how neuro-system work and has started in several model animals like fruit fly and mouse. To handle the big data of neuroimages, segmenting single-neuron morphology from raw neuroimages without losing fibers or adding noise and then tracing them for 3D reconstruction represents a key challenge.

Manual segmentation can correctly extract the single neuron images from the raw data, but it is labor-intensive and time-consuming. Thus algorithms for automatic segmentation for neuroimages were developed. A traditional segmentation method is to take an intermediate signal intensity value as a threshold directly, thereby, filter out those voxels whose signal intensity being lower than the intensity threshold directly. The traditional methods treat the importance of a voxel intuitively equivalent to its own image signal intensity or the local intensity distribution around the voxel. However, neuroimages usually do not have uniform quality because the imaging condition thereof is not identical. Therefore, there may be some voxels which are important in structure (for example the voxels which are located at the upstream branches, or at the major branch points) but have weak intensity of signal. Such voxels could be deleted in the traditional denoising and segmenting methods, which result in that the whole tree of the downstream branches of the deleted voxels disappears. Thus, the obtained tree-shaped neuron structure is incorrect. Another traditional method captures images of a sample many times, collects a number of images of different intensities of signal and combines them into a high-dynamic-range image to stabilize signal. However, such method will significantly increase the time spent for capturing the images, and damage biological tissues for imaging.

Accordingly, there is still a need for a solution which can solve the problem of the tradition technique for automatic segmentation of neuroimages.

SUMMARY

To overcome the problem of the tradition technique of incorrectness of the obtained tree-shaped neuron structure, the present invention provides a method of segmenting single neuron images with high-dynamic-range thresholds and a computer readable storage medium thereof.

In one aspect, the present invention discloses a method of segmenting single neuron images with high-dynamic-range thresholds, including: preparing a biological tissue sample containing neurons and performing single three-dimensional imaging to the biological tissue sample containing neurons to obtain a single three-dimensional raw neuroimage, the imaging technique may be but be not limited to confocal microscope fluorescent imaging, electron microscope imaging, X-ray diffraction imaging, etc; filtering out voxels in the three-dimensional raw neuroimage whose signal intensities are below a first signal intensity threshold, a second signal intensity threshold, a third signal intensity, . . . , a n-th signal intensity threshold respectively by a filtering module to obtain a first filtered image, a second filtered image, a third filtered image, . . . , a n-th filtered image; tracing the first filtered image, the second filtered image, the third filtered image, . . . , the n-th filtered image for their skeleton by a tracing module respectively to obtain a first traced image, a second traced image, a third traced image, . . . , a n-th traced image; calculating structural importance score of every voxel in the first traced image, the second traced image, the third traced image, . . . , the n-th traced image by a score calculating module respectively by utilizing an equation to obtain a first structural importance score, a second structural importance score, a third structural importance score, . . . , a n-th structural importance score of every voxel; summing up the first structural importance score, the second structural importance score, the third structural importance score, . . . , and the n-th structural importance score of every voxel by a summing module to obtain a summed structural importance score of every voxel; determining a structural importance score threshold; and filtering out voxels in the three-dimensional raw neuroimage whose summed structural importance scores are below the structural importance score threshold by the filtering module respectively to obtain a single neuron three-dimensional image.

In another aspect, the present invention discloses a non-transitory computer readable storage medium having stored thereon program instructions that, when executed by a processor, cause the processor to perform the steps of: loading a single three-dimensional raw neuroimage; filtering out voxels in the three-dimensional raw neuroimage whose signal intensities are below a first signal intensity threshold, a second signal intensity threshold, a third signal intensity threshold, . . . , a n-th signal intensity threshold respectively to obtain a first filtered image, a second filtered image, a third filtered image, . . . , a n-th filtered image; tracing the first filtered image, the second filtered image, the third filtered image, . . . , the n-th filtered image for their skeleton respectively to obtain a first traced image, a second traced image, a third traced image, . . . , a n-th traced image; calculating structural importance scores of every voxel in the first traced image, the second traced image, the third traced image, . . . , the n-th traced image respectively by utilizing an equation to obtain a first structural importance score, a second structural importance score, a third structural importance score, . . . , a n-th structural importance score of every voxel; summing up the first structural importance score, the second structural importance score, the third structural importance score, . . . , and the n-th structural importance score of every voxel to obtain a summed structural importance score of every voxel; determining a structural importance score threshold; and filtering out voxels in the three-dimensional raw neuroimage whose summed structural importance scores are below the structural importance score threshold to obtain a single neuron three-dimensional image.

One advantage of the present invention is that, in comparison with the traditional method using uniform intensity threshold, the present invention can achieve the function of reserving the voxels which are important in the global structure but have weak intensity of signal, and therefore can retain correct branch structures of the neuron.

Another advantage of the present invention is that, besides the correctness, the present invention employs algorithm to automatically segment single neuron images and thus much more efficient than manual segmentation.

These and other advantages will become apparent from the following description of preferred embodiments taken together with the accompanying drawings and the appended claims.

BRIEF DESCRIPTION OF THE DRAWINGS

The present invention may be understood by some preferred embodiments and detailed descriptions in the specification and the attached drawings below.

FIG. 5A illustrates a flow chart of a method of segmenting single neuron images with high-dynamic-range thresholds in accordance with one embodiment of the present invention.

DETAILED DESCRIPTION OF THIS DISCLOSURE

Figure 1:
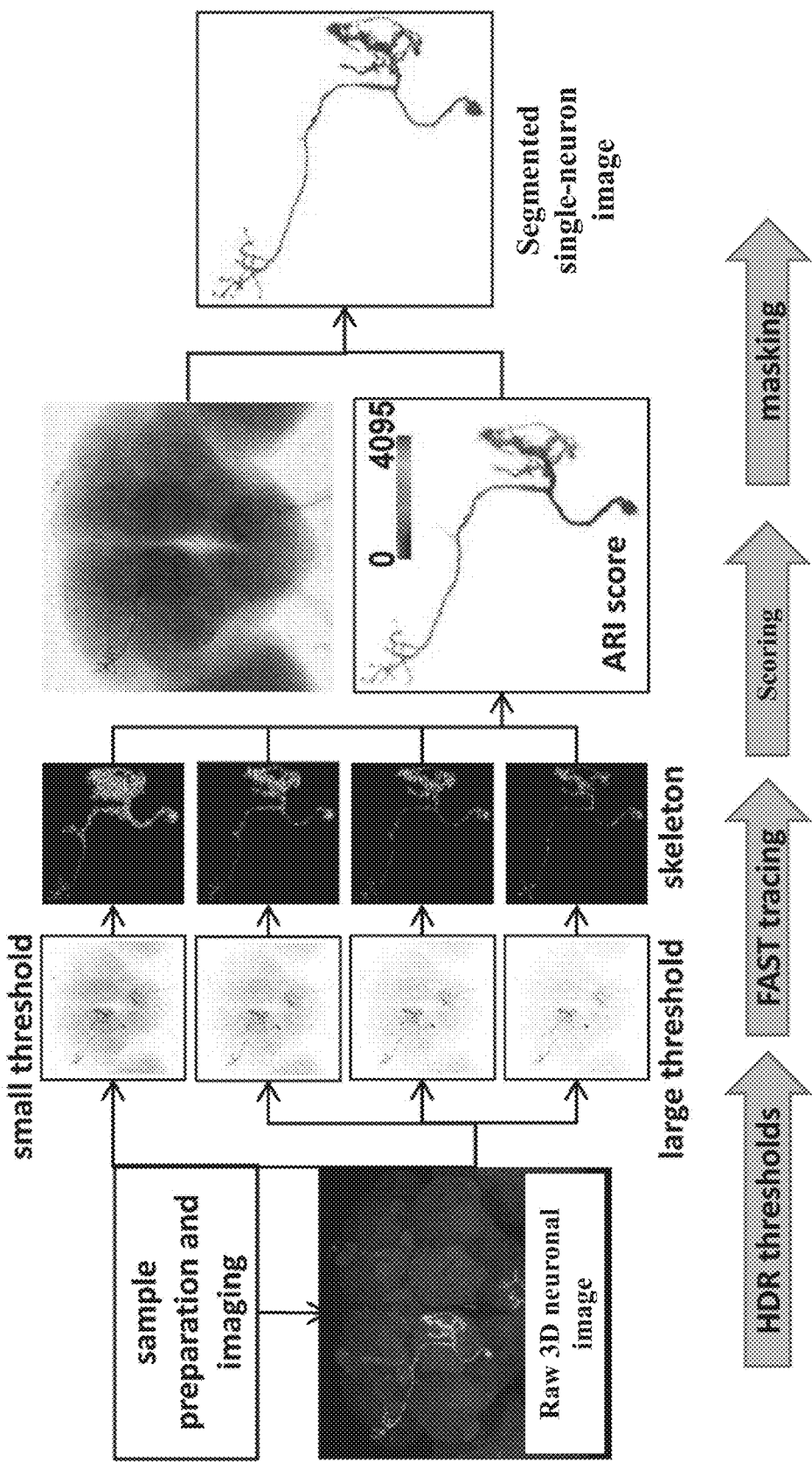
FIG. 1 illustrates a flow chart of a method of segmenting single neuron images with high-dynamic-range thresholds in accordance with a preferred embodiment of the present invention.

The present invention will now be described with the preferred embodiments and aspects and these descriptions interpret structure and procedures of the present invention only for illustrating but not for limiting the Claims of the present invention. Therefore, except the preferred embodiments in the specification, the present invention may also be widely used in other embodiments.

The present invention discloses a method of segmenting single neuron images with high-dynamic-range (HDR) thresholds. The "high dynamic range threshold" mentioned herein means that a series of signal intensity thresholds from small to large are taken for a single three-dimensional raw neuroimage, the filtered image is structurally analyzed to determine structural importance of every voxel after voxels of low intensity are filtered out, and the highest signal intensity threshold may be two order of magnitude greater than the lowest signal intensity threshold or more. Thus, such method is referred to as "high dynamic range threshold" method. In one embodiment, the method of segmenting single neuron images with high-dynamic-range thresholds can be automatic. First, a plurality of signal intensities of different values from small to large are utilized as thresholds respectively. Voxels in a three-dimensional raw neuroimage whose signal intensities are below different thresholds are filtered out respectively. Then, the filtered images are traced for its skeleton respectively. Subsequently, the traced images are performed with structural importance scoring respectively. Finally, the scores are summed up. Whether every voxel is reserved or not is determined based on its summed-up score. That is, a mask is made according to every voxel's summed-up score. If a certain voxel's summed-up score is below a predetermined value, that voxel will be deleted. On the contrary, if a certain voxel's summed-up score is above the predetermined value, that voxel will be reserved. In one embodiment, the predetermined value may be determined by the user. When a small signal intensity value is employed as the threshold, some voxels which are very important in structure but have weak intensity of signal will be reserved and those voxels will gain relatively high score when performed with structural importance scoring. Therefore, those voxels will not be deleted. However, those voxels which are very important in structure but have weak intensity of signal may be filtered out in the traditional method because the traditional method utilizes an intermediate intensity as the threshold directly. Voxels at critical positions (usually belonging to the upstream branches which were closer to the cell body) but with weak signal intensity can be deleted under such threshold and all the downstream branches will be completely lost. The method of the present invention can achieve the function of reserving the voxels which are important in structure but have weak intensity of signal, and therefore can retain correct branch structures of the neuron. Besides, the present invention employs algorithm to automatically segment single neuron images and thus can significantly save more time than a traditional method of manual segmentation. The method of segmenting single neuron images with high-dynamic-range (HDR) thresholds of the present invention has processed the data amount in about two weeks to complete the single neuron segmentation from more than 20,000 fluorescent raw images, which were collected and processed by the traditional segmentation methods for eight years.

The central concept of the present invention is that every voxel with non-zero signal intensity is assigned with a structural importance score according to its position in the global neuronal morphology under a wide range of signal intensity thresholds. The present invention evaluates the likelihood of the voxels to be a real signal from the global structure of neuroimages. In usual imaging conditions, noises appear randomly and the clusters of neighboring noises do not favor any particular shape. On the other hand, the basic feature of neuronal morphology is tree-like structure composed of quasi-one-dimensional fibers. A set of connected voxels having a big tree-like structure composed of many fibers and branching levels were very unlikely to be a random noise. Voxels in such structure should have higher probability to be real signal. Similar argument could be applied to the connected voxels which form a very long fiber.

FIG. 1 illustrates a flow chart of the method of segmenting single neuron images with high-dynamic-range thresholds in accordance with a preferred embodiment of the present invention. As shown in FIG. 1, biological tissue sample containing neurons is sampled and prepared first, and the neurons therein are dyed by utilizing for instance but not limited to fluorescent dyes and are three-dimensionally imaged by employing for example but not limited to confocal microscope to obtain a three-dimensional raw neuroimage of a biological tissue sample containing neurons. Subsequently, the soma position(s) in the three-dimensional raw neuroimage is detected for instance based on the shape of the maximal ellipsoid-like clusters of voxels. In one embodiment, the step of detecting the soma position(s) in the three-dimensional raw neuroimage may be automatic. Then, the three-dimensional raw neuroimage is segmented (filtered) with a minimal signal intensity threshold such as a first signal intensity threshold $t_1$. That is, the voxels in the three-dimensional raw neuroimage whose signal intensity is below the minimal signal intensity threshold such as the first signal intensity threshold $t_1$ are filtered out. Subsequently, this first segmented (filtered) three-dimensional neuroimage is traced for its skeleton by utilizing for instance but not limited to FAST (fast automatically structural tracing). Then, at the j-th signal intensity threshold $t_j$, the structural importance scores of the voxels with the non-zero signal intensity are calculated by employing an equation to obtain a first structural importance score. In one embodiment, the equation may be but be not limited to:

$$a_i^{(j)} = \max([G_i^{(j)} - G_0^{(j)}], 0) + \left\lfloor \frac{N_i^{(j)}}{N_0^{(j)}} \right\rfloor + \left\lfloor \frac{L_i^{(j)}}{L_0^{(j)}} \right\rfloor + \lambda_i^{(j)}$$

$$\text{wherein } G_0^{(j)} = \max\left(\left\lceil G_0^{(1)} \times \left(1 - \frac{t_j}{t_{max}}\right)\right\rceil, 1\right),$$

wherein $\lfloor \ \rfloor$ and $\lceil \ \rceil$ are respectively the Gaussian floor and ceil functions, $L_i^{(j)}$ is the length of the i-th branch, $N_i^{(j)}$ is the number of offspring branches of the i-th branch, $G_i^{(j)}$ is the number of offspring generation of the i-th branch, i.e. how many generations of the offsprings the i-th branch have, $G_0^{(1)}$ is at the minimal signal intensity threshold equaled to the 75 percentile of the number of the non-zero $G_i^{(j=1)}$, if this value is less than 20, $G_0^{(1)}=20$ is set, $a_i^{(j)}$ is the structural importance score of the i-th branch after j-th segmentation, also referred to as arborization robustness index (ARI), $t_j$ is the j-th signal intensity threshold, $t_{max}$ is the maximal signal intensity threshold for all signal intensity thresholds t, $N_0^{(j)}=3G_0^{(j)}$, $L_0=6$ micrometers.

$$\lambda_i^{(j)} = \max\left(\left\lfloor \frac{L_p^{(j)}}{L_0^{(j)}} \right\rfloor, \text{ for } p \in \Lambda_i^{(j)}, G_i^{(j)} < G_0^{(j)} \text{ and } N_i^{(j)} < N_0^{(j)}\right)$$

is the score obtained from the length of the longest downstream branch of i-th branch under the j-th signal intensity threshold $t_j$, where $\Lambda_i^{(j)}$ is a set formed by all downstream branches of the i-th branch under the j-th signal intensity threshold $t_j$, p is any one branch belonging to the $\Lambda_i^{(j)}$ set. The condition $G_i^{(j)}<G_0^{(j)}$ and $N_i^{(j)}<N_0^{(j)}$ for the last term means that if $G_i^{(j)} \geq G_0^{(j)}$ or $N_i^{(j)} \geq N_0^{(j)}$, this branch will gain score and will not get additional score from the length of the downstream long branches. We need the last term because when the i-th branch originally does not gain score at the j-th signal intensity threshold (i.e. $G_i^{(j)}<G_0^{(j)}$ and $N_i^{(j)}<N_0^{(j)}$) but the downstream p-th branch gains score because the downstream p-th branch is long enough to be identified as real signal, the i-th branch will also gain score because the downstream p-th branch gains score. This term can avoid happening that the downstream p-th branch gains score while the upstream i-th branch does not gain score, which results in that the global tree-like neuron is cut off and lacks complete connection. The $N_0^{(j)}$, $G_0^{(j)}$ and $L_0$ are adjustable parameters in accordance with one embodiment and can be adjusted according to imaging conditions when actually utilized.

Subsequently, the three-dimensional raw neuroimage is segmented (filtered) with a second signal intensity threshold $t_2$ which is slightly larger than the minimal signal intensity threshold. That is, the voxels in the three-dimensional raw neuroimage whose signal intensity is below the second signal intensity threshold $t_2$ are filtered out. Then, the second segmented (filtered) three-dimensional neuroimage is traced for its skeleton by utilizing for instance but not limited to FAST (fast automatically structural tracing). Subsequently, the structural importance scores of the voxels with the non-zero signal intensity are calculated by employing the equation to obtain a second structural importance score. Then, the three-dimensional raw neuroimage is segmented (filtered) with a third signal intensity threshold $t_3$ which is slightly larger than the second signal intensity threshold. That is, the voxels in the three-dimensional raw neuroimage whose signal intensity is below the third signal intensity threshold $t_3$ are filtered out. Subsequently, the third segmented (filtered) three-dimensional neuroimage is traced for its skeleton by utilizing for instance but not limited to FAST (fast automatically structural tracing). Then, the structural importance scores of the voxels with the non-zero signal intensity are calculated by employing the equation to obtain a third structural importance score.

In the same way, the three-dimensional raw neuroimage is segmented (filtered) with a fourth signal intensity threshold $t_4$, a fifth signal intensity threshold $t_5$, . . . , a n-th signal intensity threshold $t_n$ (also referred to as a maximal signal intensity threshold $t_{max}$), respectively. That is, the voxels in the three-dimensional raw neuroimage whose signal intensity is below the fourth signal intensity threshold $t_4$, the fifth signal intensity threshold $t_5$, . . . , the n-th signal intensity threshold $t_n$ respectively are filtered out. In one embodiment, the intervals and the ranges among the first signal intensity threshold $t_1$, the second signal intensity threshold $t_2$, the third signal intensity threshold $t_3$, the fourth signal intensity threshold $t_4$, the fifth signal intensity threshold $t_5$, . . . , the n-th signal intensity threshold $t_n$ may be determined based on the property or the quality of the three-dimensional raw neuroimage. In one embodiment, the interval $t_{step}$ among the first signal intensity threshold $t_1$, the second signal intensity threshold $t_2$, the third signal intensity threshold $t_3$, the fourth signal intensity threshold $t_4$, the fifth signal intensity threshold $t_5$, . . . , the n-th signal intensity threshold $t_n$ may be but be not limited to 2 (for 8-bit images) or 10 (for 12-bit images). In one embodiment, n may be but be not limited to 50. In one embodiment, the dynamic range $R_D$ of the aforementioned signal intensity thresholds may be but be not limited to 10 or 500. Subsequently, the segmented (filtered) three-dimensional neuroimages are traced for its skeleton by utilizing for instance but not limited to FAST (fast automatically structural tracing), respectively. Then, the structural importance scores of the voxels with the non-zero signal intensity are calculated by employing the equation respectively to obtain a fourth structural importance score, a fifth structural importance score, . . . , a n-th structural importance score respectively. Subsequently, the first structural importance score, the second structural importance score, the third structural importance score, the fourth structural importance score, the fifth structural importance score, . . . , and the n-th structural importance score may be summed up for every voxel with non-zero signal intensity, so as to obtain a summed structural importance score for a certain voxel.

Then, a structural importance score threshold, also referred to as a mask m, is determined according to the summed structural importance score. In one embodiment, the structural importance score threshold may be determined by the user. Subsequently, the three-dimensional raw neuroimage is segmented (filtered) with the structural importance score threshold. That is, the voxels in the three-dimensional raw neuroimage whose summed structural importance score is below the structural importance score threshold are filtered out because a voxel is deemed to be noise if its summed structural importance score is below the structural importance score threshold. Then, the segmented (filtered) three-dimensional neuroimage is traced for its skeleton by utilizing for instance but not limited to FAST (fast automatically structural tracing) to obtain a single neuron reconstructed image.

Fast automatically structural tracing is a powerful tracing algorithm to extract the structure features from volumes of data. "Source field" of the voxels in the image are encoded according to their shortest path lengths from the starting point, i. e., soma of the neuron. A "codelet" is launched from the soma and travels along the direction of increasing source field. Voxels with source field between i−1 and i+1 belong to the i-th position of the codelet. The codelet travels through the connected voxels by increasing i. When the codelet splits into two codelets and starts to trace the two new branches individually from the two new starting points (respective centers of mass of the two new codelets). The codelets stops at the next branching points or the end points of the neuron. The trajectory of the center of mass of the codelets defines central points of the branch. The central point at the position where the codelet splits defines the branch point. A local tracing procedure is performed to 1) move the branching point back from the edge of the image to an interior point on the central line, and 2) to fill the gap between the new branching point and the starting points of the two downstream branches with additional central points. The final results of FAST show the partition of branches, starting point of each branch, branching point, endpoints, and skeleton of the neuron.

Therefore, FAST provides positions of all the key points in the skeleton of each neuron (including branching points, central points and end points) and the hierarchical information for each branch of the traced neuron. The detailed technical content of FAST may refer to U.S. patent application Pub. No. 2011/0157177, which is incorporated herein by reference in its entirety. The first fiber projected from the soma is the primary neurite with the generation G=1. The terminal other than the soma of the primary neurite will be a branch point, and also the starting points of G=2 neurites. The branches started from the branch point of the upstream neurite (with generation G) are called the daughter neurites of the upstream or parent neurite and with generation G+1. The daughter neurites are offsprings of the parent neurite, as well as all the offsprings of the daughter neurites. The voxels of the branches with $G_i^{(j)}$ larger than $G_0^{(j)}$, $N_i^{(j)}$ larger than $N_0^{(j)}$, or length $L_i^{(j)}$ longer than $L_0$ will have higher probabilities to survive during the HDR FAST process, where the tuning parameters $G_0^{(j)}$, $N_0^{(j)}$ and $L_0$ set the criteria to evaluate the likelihood of the voxels to be real signals. As the signal intensity threshold $t_j$ increases, $G_0^{(j)}$ decreases accordingly because more branches will be eliminated at higher signal intensity threshold and all $G_i^{(j)}$ will be decreased. Also, voxels with higher signal intensity can survive under higher signal intensity thresholds, and have the opportunity to gain more ARI. Thus, ARI can effectively represent both the original signal intensity and the importance of each voxel in the global neuronal morphology, rather than only its original signal intensity in the three-dimensional raw neuroimage in the traditional methods.

Figure 2:
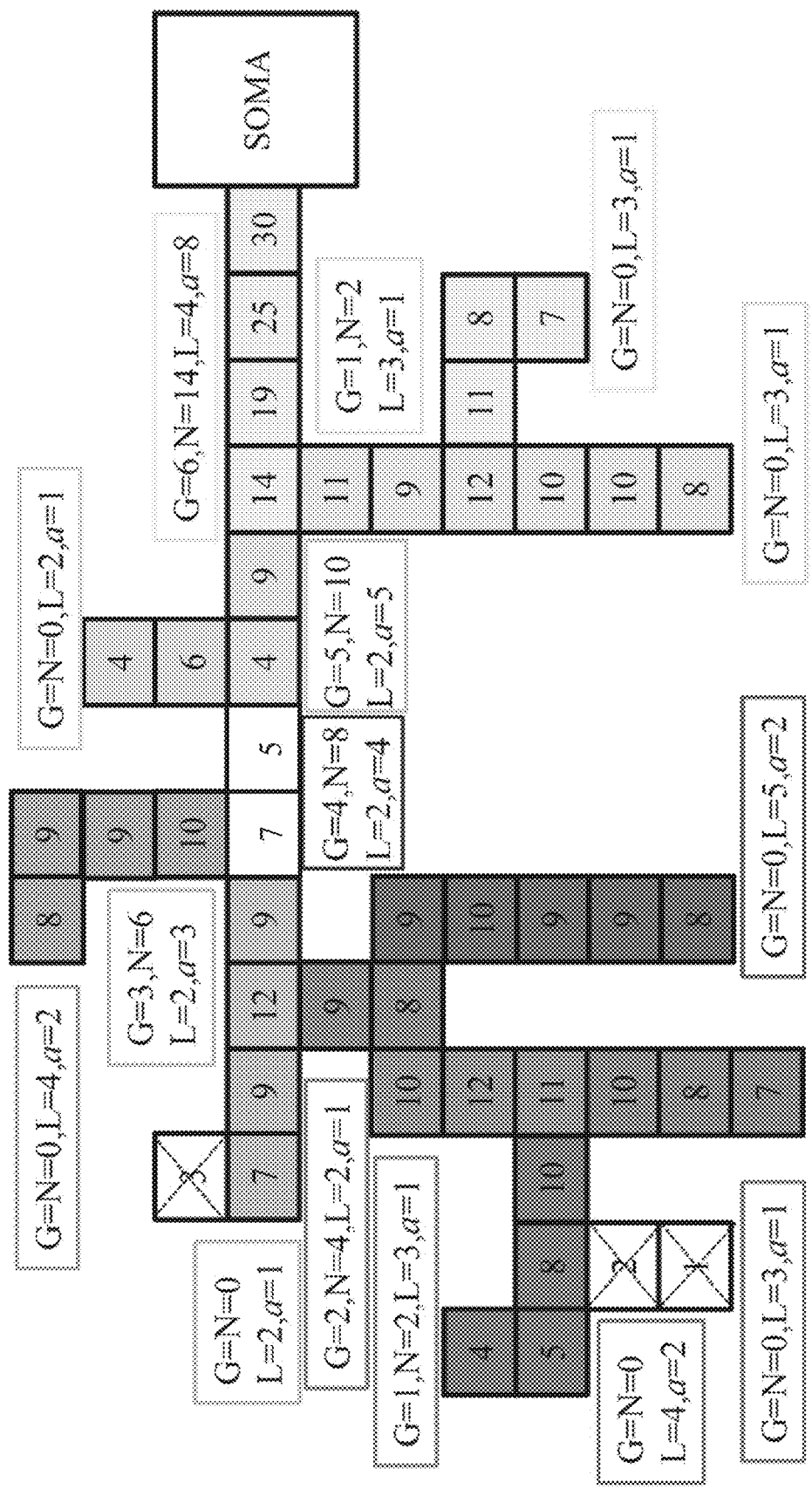
FIG. 2 illustrates a diagram of a schematic example of structural importance score calculation for a certain signal intensity threshold in accordance with one embodiment of the present invention.
Figure 3:
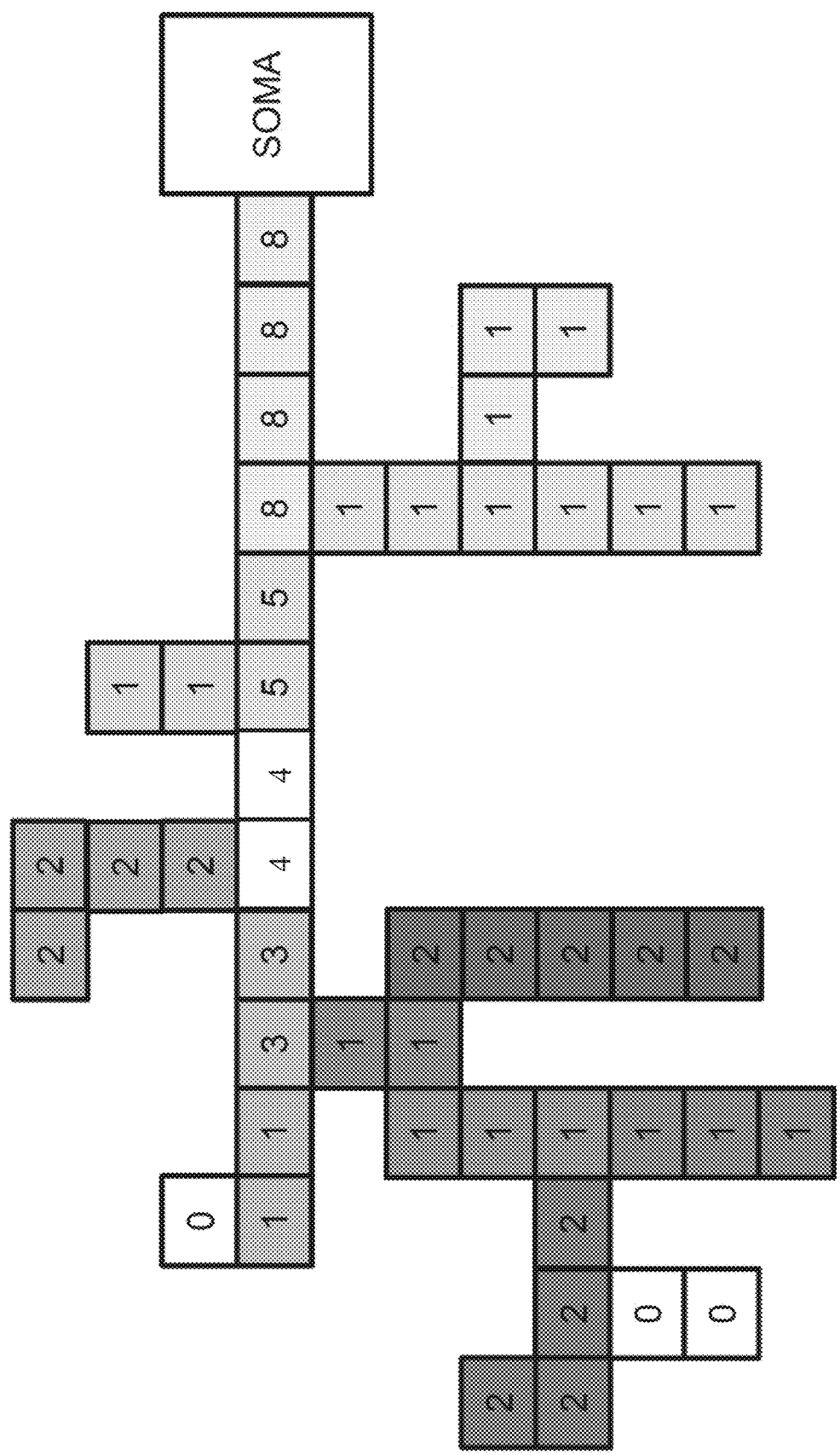
FIG. 3 illustrates a diagram showing structural importance scores calculated for every voxel in FIG. 2 for a certain signal intensity threshold in accordance with one embodiment of the present invention.

FIG. 2 illustrates a diagram of a schematic example of structural importance score calculation in accordance with one embodiment of the present invention. In this embodiment, $G_0=L_0=2$, $N_0=3G_0=6$, and the signal intensity threshold t=4. The numbers in the boxes represent the original signal intensity of each voxel. The values of parameters G, N and L and the obtained structural importance score a are listed adjacent to the boxes. FIG. 3 illustrates structural importance scores calculated for every voxel in FIG. 2 for a certain time in accordance with one embodiment of the present invention. The numbers in the boxes represent the structural importance score, i.e. ARI, of each voxel.

The present invention may include various processes. The processes of the present invention may be performed by hardware components or software components which may be used to cause a general purpose or special purpose processor or logic circuits programmed with the instructions to perform the processes. Alternatively, the processes may be performed by a combination of hardware and software.

Figure 4:
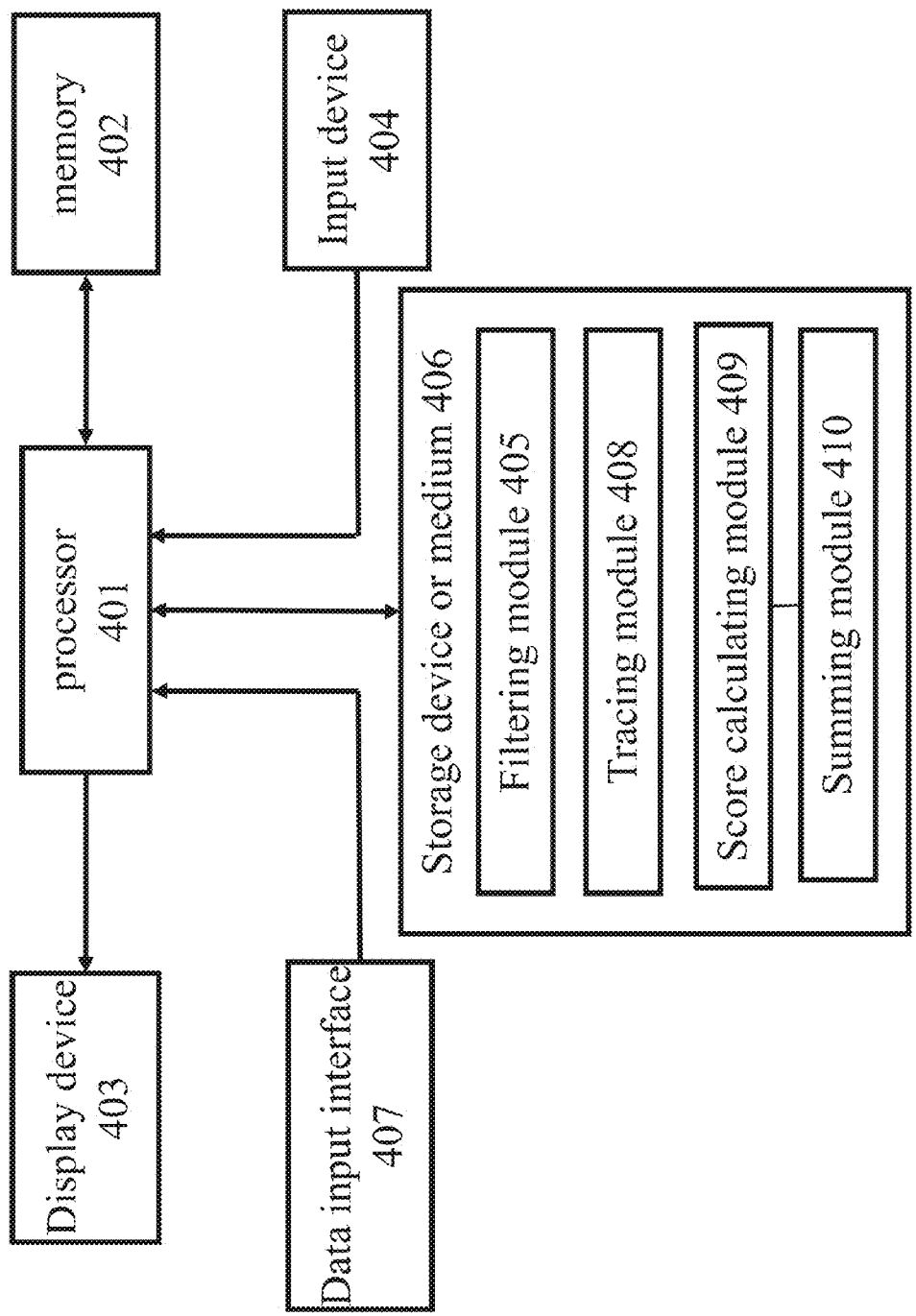
FIG. 4 illustrates a block diagram of an example of a computing device cooperated with a method of segmenting single neuron images with high-dynamic-range thresholds of the present invention in accordance with one embodiment of the present invention.

With reference to FIG. 4, the method of segmenting single neuron images with high-dynamic-range thresholds of the present invention may be performed in a storage device or medium 406 of a computing device in FIG. 4. The method of segmenting single neuron images with high-dynamic-range thresholds may be implemented by the cooperation of the processor 401 with other components. Portions of the present invention may be provided as a program product, which may include a computer readable storage medium having stored thereon program instructions, which may be used to program a processor (or other electronic devices) to perform a process according to the present invention. The computer readable storage medium may include, but is not limited to, ROMs (read only memory), RAMs (random access memory), EPROMs (erasable programmable read-only memory), EEPROMs (electrically erasable programmable read-only memory), flash memory, or other type of computer readable storage medium suitable for storing electronic instructions.

To achieve the objects of the present invention, the method of segmenting single neuron images with high-dynamic-range thresholds of the present invention may cooperate with the computing device exemplarily shown in FIG. 4 to perform or execute related instructions. The computing device is shown for illustrating the present invention, not for limiting the present invention. As shown in FIG. 4, the computing device includes a processor 401, a memory 402 electrically coupled to the processor 401, and a display device 403 electrically coupled to the processor 401 to display information. An input device 404 is electrically coupled to the processor 401 to input instructions. For example, the input device 404 may include a keyboard or a touch panel. A storage device or medium 406, which may include ROM, RAM, EPROM, EEPROM, flash memory or nonvolatile memory, is electrically coupled to the processor 401. The storage device or medium 406 may store a filtering module 405, a tracing module 408, a score calculating module 409 and a summing module 410. A data input interface 407, which may include a wired data input interface and a wireless data input interface, is electrically coupled to the processor 401. The wired data input interface may include universal serial bus. The wireless data input interface may include BLUETOOTH and IR (infrared).

Figure 5B:
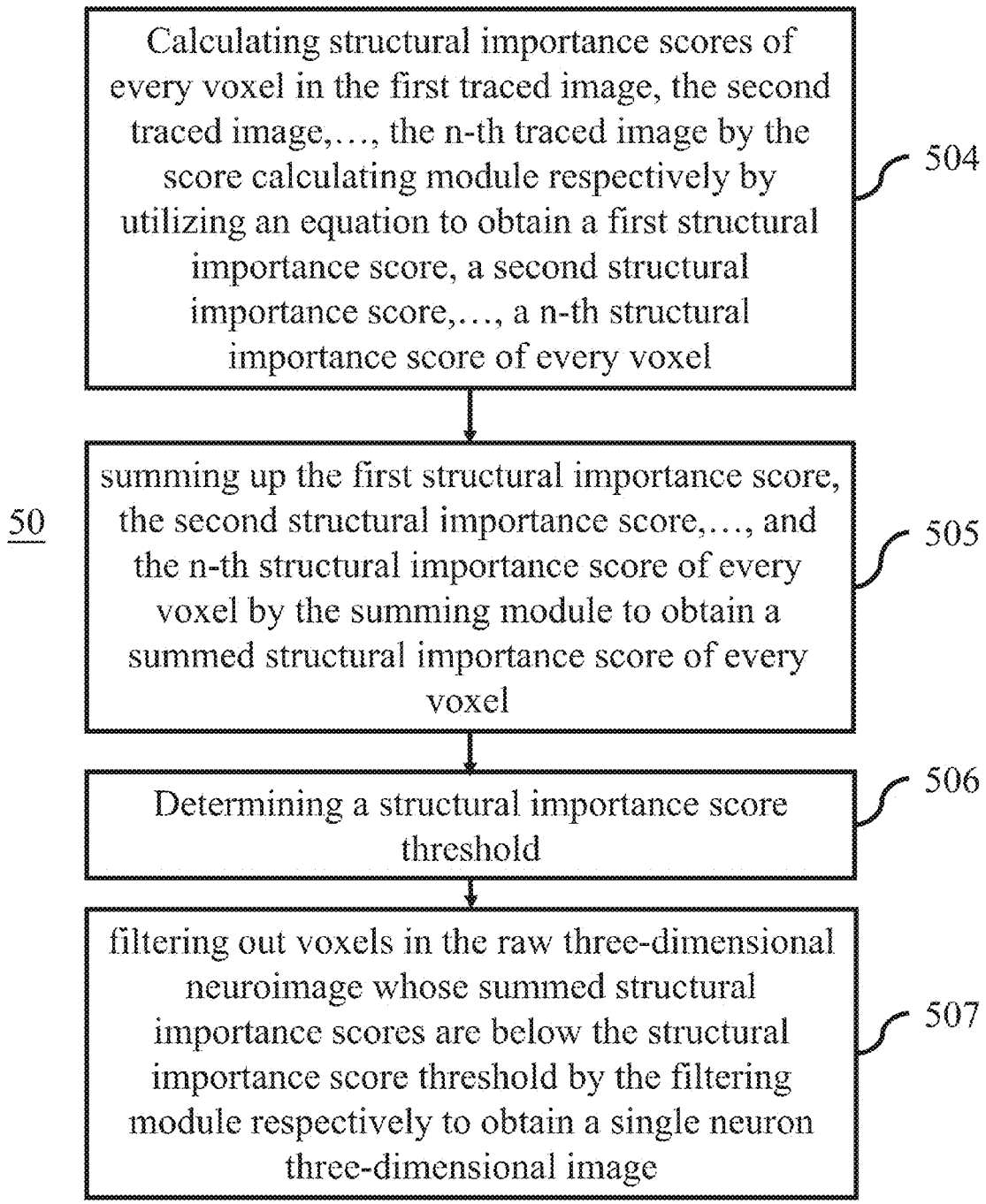
FIG. 5B illustrates a flow chart of a method of segmenting single neuron images with high-dynamic-range thresholds in accordance with one embodiment of the present invention.

Please refer to FIGS. 5A and 5B, which illustrate flow charts of a method of segmenting single neuron images with high-dynamic-range thresholds in accordance with one embodiment of the present invention. As shown in FIG. 5A, the method 500 of segmenting single neuron images with high-dynamic-range thresholds of the present invention includes preparing a biological tissue sample containing neurons and performing single three-dimensional imaging to the biological tissue sample containing neurons to obtain a single three-dimensional raw neuroimage in step 501. Then, in step 502, voxels in the three-dimensional raw neuroimage whose signal intensities are below a first signal intensity threshold, a second signal intensity threshold, . . . , a n-th signal intensity threshold respectively are filtered out by the filtering module 405 respectively to obtain a first filtered image, a second filtered image, . . . , a n-th filtered image. Subsequently, in step 503, the first filtered image, the second filtered image, . . . , the n-th filtered image are traced for their skeleton by the tracing module 408 respectively to obtain a first traced image, a second traced image, . . . , a n-th traced image. As shown in FIG. 5B, then in step 504, structural importance scores of every voxel in the first traced image, the second traced image, . . . , the n-th traced image are calculated by the score calculating module 409 respectively by utilizing an equation to obtain a first structural importance score, a second structural importance score, . . . , a n-th structural importance score of every voxel. Subsequently, in step 505, the first structural importance score, the second structural importance score, . . . , and the n-th structural importance score of every voxel are summed up by the summing module 410 to obtain a summed structural importance score of every voxel. Then, in step 506, a structural importance score threshold is determined. Subsequently, in step 507, voxels in the three-dimensional raw neuroimage whose summed structural importance scores are below the structural importance score threshold are filtered out by the filtering module 405 respectively to obtain a single neuron three-dimensional image, wherein n is a positive integer which is larger than 3. In one embodiment, n may be but be not limited to 50.

The foregoing description is a preferred embodiment of the present invention. It should be appreciated that this embodiment is described for purposes of illustration only, not for limiting, and that numerous alterations and modifications may be practiced by those skilled in the art without departing from the spirit and scope of the present invention. It is intended that all such modifications and alterations are included insofar as they come within the scope of the present invention as claimed or the equivalents thereof.

What is claimed is:

1. A method of segmenting single neuron images with high-dynamic-range thresholds, comprising:
preparing a biological tissue sample containing neurons and performing single three-dimensional imaging to said biological tissue sample containing neurons to obtain a single three-dimensional raw neuroimage;
filtering out voxels in said three-dimensional raw neuroimage whose signal intensities are below a first signal intensity threshold, a second signal intensity threshold, . . . , a n-th signal intensity threshold respectively by a filtering module to obtain a first filtered image, a second filtered image, . . . , a n-th filtered image;
tracing said first filtered image, said second filtered image, . . . , said n-th filtered image for their skeleton by a tracing module respectively to obtain a first traced image, a second traced image, . . . , a n-th traced image;
calculating structural importance scores of every voxel in said first traced image, said second traced image, . . . , said n-th traced image by a score calculating module respectively by utilizing an equation to obtain a first structural importance score, a second structural importance score, . . . , a n-th structural importance score of every voxel;
summing up said first structural importance score, said second structural importance score, . . . , and said n-th structural importance score of every voxel by a summing module to obtain a summed structural importance score of every voxel;
determining a structural importance score threshold; and
filtering out voxels in said three-dimensional raw neuroimage whose summed structural importance scores are below said structural importance score threshold by said filtering module to obtain a single neuron three-dimensional image, wherein n is a positive integer which is larger than 3.

2. The method of claim 1, before the step of filtering out voxels in said three-dimensional raw neuroimage whose signal intensities are below a first signal intensity threshold, a second signal intensity threshold, . . . , a n-th signal intensity threshold respectively, further comprising detecting soma position in said three-dimensional raw neuroimage.

3. The method of claim 1, wherein said equation comprises:

$$a_i^{(j)} = \max([G_i^{(j)} - G_0^{(j)}], 0) + \left\lfloor \frac{N_i^{(j)}}{N_0^{(j)}} \right\rfloor + \left\lfloor \frac{L_i^{(j)}}{L_0^{(j)}} \right\rfloor + \lambda_i^{(j)}$$

$$\text{wherein } G_0^{(j)} = \max\left(\left\lceil G_0^{(1)} \times \left(1 - \frac{t_j}{t_{max}}\right)\right\rceil, 1\right),$$

wherein $\lfloor\ \rfloor$ and $\lceil\ \rceil$ are respectively Gaussian floor and ceil functions, $L_i^{(j)}$ is length of i-th branch, $N_i^{(j)}$ is number of offspring branches of the i-th branch, $G_i^{(j)}$ is number of offspring generation of the i-th branch, $G_i^{(1)}$ is at minimal signal intensity threshold equaled to a 75 percentile of a number of non-zero $G_i^{(j=1)}$, if this value is less than 20, $G_0^{(1)}=20$ is set, $a_i^{(j)}$ is structural importance score of the i-th branch after j-th segmentation, $t_j$ is j-th signal intensity threshold, $t_{max}$ is maximal signal intensity threshold for all signal intensity thresholds t, $N_0^{(j)}=3G_0^{(j)}$, $L_0=6$ micrometers.

$$\lambda_i^{(j)} = \max\left(\left\lfloor \frac{L_p^{(j)}}{L_0^{(j)}} \right\rfloor, \text{ for } p \in \Lambda_i^{(j)}, G_i^{(j)} < G_0^{(j)} \text{ and } N_i^{(j)} < N_0^{(j)}\right)$$

is a score obtained from a length of longest downstream branch of the i-th branch under the j-th signal intensity threshold $t_j$, where $\Lambda_i^{(j)}$ is a set formed by all downstream branches of the i-th branch under the j-th signal intensity threshold $t_j$, p is any one branch belonging to the $\Lambda_i^{(j)}$ set.

4. The method of claim 1, wherein said tracing comprises fast automatically structural tracing.

5. The method of claim 1, wherein the step of determining a structural importance score threshold is based on said summed structural importance score of every voxel.

6. The method of claim 1, wherein intervals among said first signal intensity threshold, said second signal intensity threshold, . . . , said n-th signal intensity threshold are determined from a quality of said single three-dimensional raw neuroimage.

7. The method of claim 1, wherein n includes 50.

8. A non-transitory computer readable storage medium having stored thereon program instructions that, when executed by a processor, cause said processor to perform the steps of:
loading a single three-dimensional raw neuroimage;
filtering out voxels in said three-dimensional raw neuroimage whose signal intensities are below a first signal intensity threshold, a second signal intensity threshold, . . . , a n-th signal intensity threshold respectively to obtain a first filtered image, a second filtered image, . . . , a n-th filtered image;
tracing said first filtered image, said second filtered image, . . . , said n-th filtered image for their skeleton respectively to obtain a first traced image, a second traced image, . . . , a n-th traced image;
calculating structural importance scores of every voxel in said first traced image, said second traced image, . . . , said n-th traced image respectively by utilizing an equation to obtain a first structural importance score, a second structural importance score, . . . , a n-th structural importance score of every voxel;
summing up said first structural importance score, said second structural importance score, . . . , and said n-th structural importance score of every voxel to obtain a summed structural importance score of every voxel;
determining a structural importance score threshold; and
filtering out voxels in said three-dimensional raw neuroimage whose summed structural importance scores are below said structural importance score threshold to obtain a single neuron three-dimensional image, wherein n is a positive integer which is larger than 3.

9. The non-transitory computer readable storage medium of claim 8, before the step of filtering out voxels in said three-dimensional raw neuroimage whose signal intensities are below a first signal intensity threshold, a second signal intensity threshold, . . . , a n-th signal intensity threshold respectively, further comprising detecting soma position in said three-dimensional raw neuroimage.

10. The non-transitory computer readable storage medium of claim 8, wherein said equation comprises:

$$a_i^{(j)} = \max([G_i^{(j)} - G_0^{(j)}], 0) + \left\lfloor \frac{N_i^{(j)}}{N_0^{(j)}} \right\rfloor + \left\lceil \frac{L_i^{(j)}}{L_0^{(j)}} \right\rceil + \lambda_i^{(j)}$$

$$\text{wherein } G_0^{(j)} = \max\left(\left\lceil G_0^{(1)} \times \left(1 - \frac{t_j}{t_{max}}\right)\right\rceil, 1\right),$$

wherein $\lfloor \ \rfloor$ and $\lceil \ \rceil$ are respectively Gaussian floor and ceil functions, $L_i^{(j)}$ is length of i-th branch, $N_i^{(j)}$ is number of offspring branches of the i-th branch, $G_i^{(j)}$ is number of offspring generation of the i-th branch, $G_0^{(1)}$ is at minimal signal intensity threshold equaled to a 75 percentile of a number of non-zero $G_i^{(j=1)}$, if this value is less than 20, $G_0^{(1)}=20$ is set, $a_i^{(j)}$ is structural importance score of the i-th branch after j-th segmentation, $t_j$ is j-th signal intensity threshold, $t_{max}$ is maximal signal intensity threshold for all signal intensity thresholds t, $N_0^{(j)}=3G_0^{(j)}$, $L_0=6$ micrometers.

$$\lambda_i^{(j)} = \max\left(\left\lceil \frac{L_p^{(j)}}{L_0^{(j)}} \right\rceil, \text{ for } p \in \Lambda_i^{(j)}, G_i^{(j)} < G_0^{(j)} \text{ and } N_i^{(j)} < N_0^{(j)}\right)$$

is a score obtained from a length of longest downstream branch of the i-th branch under the j-th signal intensity threshold $t_j$, where $\Lambda_i^{(j)}$ is a set formed by all downstream branches of the i-th branch under the j-th signal intensity threshold $t_j$, p is any one branch belonging to the $\Lambda_i^{(j)}$ set.

11. The non-transitory computer readable storage medium of claim 8, wherein said tracing comprises fast automatically structural tracing.

12. The non-transitory computer readable storage medium of claim 8, wherein the step of determining a structural importance score threshold is based on said summed structural importance score of every voxel.

13. The non-transitory computer readable storage medium of claim 8, wherein intervals among said first signal intensity threshold, said second signal intensity threshold, . . . , said n-th signal intensity threshold are determined from a quality of said single three-dimensional raw neuroimage.

14. The non-transitory computer readable storage medium of claim 8, wherein n includes 50.

* * * * *